United States Patent [19]

Burg

[11] Patent Number: 4,598,840

[45] Date of Patent: Jul. 8, 1986

[54] SNAP-IN CARTRIDGE DILUTER

[76] Inventor: Donald E. Burg, 15840 SW. 84 Ave., Miami, Fla. 33157

[21] Appl. No.: 540,291

[22] Filed: Oct. 11, 1983

[51] Int. Cl.$^4$ .......................... B67D 5/52; B01L 3/02
[52] U.S. Cl. ..................................... 222/135; 222/263; 222/327; 222/333; 73/864.12; 73/864.16
[58] Field of Search .......... 73/864.02, 864.11–864.14, 73/864.16–864.18, 864.22; 285/316; 422/100; 222/23, 129, 135, 137, 145, 153, 252, 263, 280, 282, 325–327, 333, 378, 288, 386, 504

[56] References Cited

U.S. PATENT DOCUMENTS

| | | | |
|---|---|---|---|
| 2,966,175 | 12/1960 | Hyde | 141/27 |
| 3,032,359 | 5/1962 | Cator | 285/316 X |
| 3,138,290 | 1/1964 | Coulter | 222/26 |
| 3,242,881 | 3/1966 | Schafer | 222/333 X |
| 3,419,051 | 12/1968 | Gustafson et al. | 141/69 |
| 3,446,400 | 5/1969 | Hobbs et al. | 222/134 |
| 3,567,398 | 3/1971 | Farr | 422/100 |
| 3,748,911 | 7/1973 | Rousselet et al. | 73/864.22 |
| 3,800,984 | 4/1974 | Phelan | 422/100 |
| 3,915,651 | 10/1975 | Nishi | 222/333 X |
| 3,924,654 | 12/1975 | Buller et al. | 137/322 |
| 3,931,915 | 1/1976 | Downings et al. | 222/327 |
| 3,955,930 | 5/1976 | Shapiro | 222/135 X |
| 3,982,667 | 9/1976 | Chen | 222/327 X |
| 4,101,283 | 7/1978 | Sundstrom | 73/864.16 X |
| 4,155,490 | 5/1979 | Glenn | 222/327 |
| 4,223,558 | 9/1980 | Schmider et al. | 74/421 R |
| 4,241,018 | 12/1980 | Lang | 422/75 |
| 4,429,583 | 2/1984 | Watanabe et al. | 73/864.12 |
| 4,471,888 | 9/1984 | Herb et al. | 222/137 |
| 4,475,666 | 10/1984 | Bilbrey et al. | 222/14 |

*Primary Examiner*—Joseph J. Rolla
*Assistant Examiner*—Michael S. Huppert
*Attorney, Agent, or Firm*—Robert J. Van Der Wall

[57] ABSTRACT

A precision fluid dilution device intended primarily for handling precisely sized fluid samples and diluting such samples with preset volumes of a diluent, such as a chemical reagent, in which the diluent is contained in a removable valveless fluid cartridge that normally uses separate piston cylinders and pistons therein disposed for sampling and for diluent delivery. Sample pickup and diluent delivery is preferably accomplished in a tubular fluid passageway attached to the cartridge, such tubular passageway terminating in an open end after passing through a hand probe in most instances. Sample pickup is accomplished by inserting the tubular passageway open end into a sample fluid, withdrawing the sample piston a precise distance thereby aspirating a known amount of sample fluid into the tubular passageway. An accurate amount of diluent is then dispensed along with the sample. In addition to dilution of samples, this device may be used for dispensing reagent or other fluids only, pipeting a series of samples, and for pickup and discharge of reagents or other fluids with the tubular passageway. Piston actuation in the preferred embodiment is done by digital linear actuator motors that also provide the force to release the cartridge. The pistons disconnect and remain in separate piston cylinders in the cartridge upon removal of the cartridge. The readily changed self contained fluid cartridge requires no high maintenance contaminating valves or separate reagent reservoirs. An alternative embodiment is a single piston version herein described which is primarily intended for the dispensing of reagents only.

50 Claims, 5 Drawing Figures

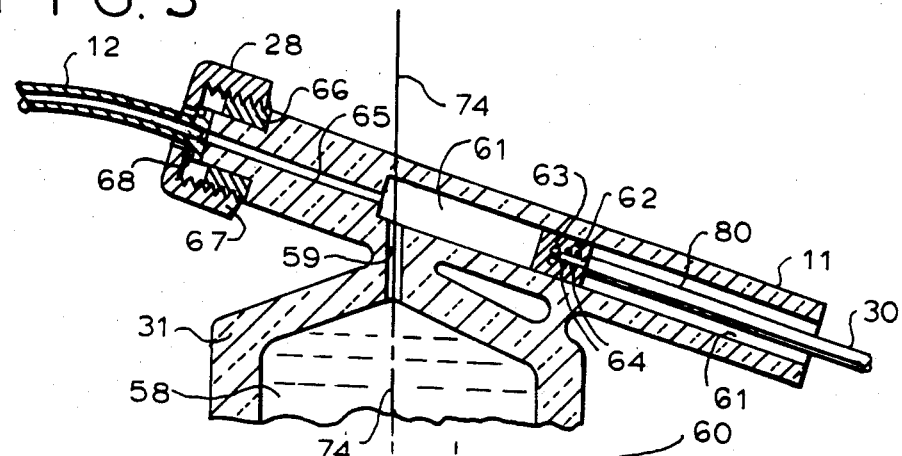
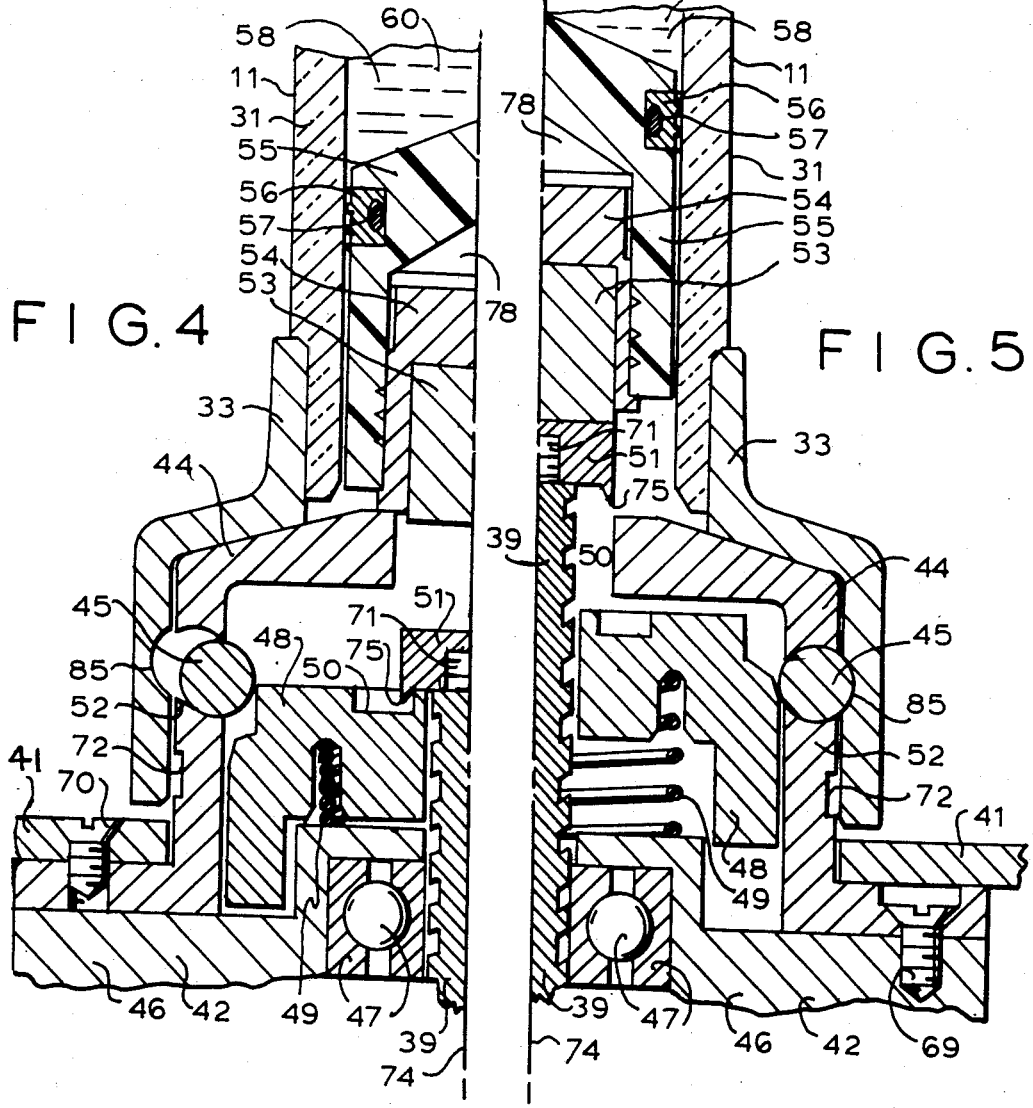

SNAP-IN CARTRIDGE DILUTER

FIELD OF THE INVENTION

This invention relates to the field of precision fluid pumping devices used primarily for diluting and dispensing of fluid samples and chemical reagents, and more particularly to the type of dilutor or dispenser having a removable fluid containing cartridge.

BACKGROUND OF THE INVENTION

This invention constitutes a significant improvement in diluting and dispensing devices used primarily for preparing samples in clinical laboratories, industrial laboratories, or anywhere that precision fluid measurement and delivery is required. Heretofore, commercially available reagent containing diluting devices have required separate reagent reservoirs, but normally feed a reagent pump through a valve or other sealing means. The valve opens to a separate reagent reservoir allowing the reagent pump, normally a syringe, to cycle and fill with reagent. The valve then rotates to its discharge postion and the pump discharges the reagent, along with the sample picked up separately if in a sample dilution mode. Discharge is normally through a tube into the test receptacle.

New technology diluters having advanced electronics and programming capabilities have recently been marketed but have remained tied with old pumping technology using valves and separate reservoirs. This use of old pumping technology imposes a severe penalty on these new units whose great flexibility in programming is thus not truly realized because the operator is limited to the reagent that is already in the system. Changeover to a new reagent requires considerable time and effort to clean out all the components in contact with the old reagent including the reservoir, valves, pumps and the like. The valve itself is, of course, a source of contamination, is usually a high maintenance item, and one result is inaccuracies in measurement. Open reagent reservoirs are also subject to contamination.

Some of the prior art includes dispensing devices having a removable, single cylinder, liquid filled syringe as illustrated by Glenn, U.S. Pat. No. 4,155,490, and Downings, et al., U.S. Pat. No. 3,931,915. Since the foregoing are limited to one large reagent piston, they are normally not satisfactory for operation at sample volumes at the low end of the scale, i.e. 2 to 5 microliters. Such devices probably have lower limits in the 50 microliter range. Therefore, Glenn and Downings, et al. must be considered as usable primarily for dispensing of reagents only. Another reference, Chen, U.S. Pat. No. 3,982 667, shows a removable reagent syringe diluter with concentric sample and reagent pistons whereby the sample piston actually passes through a seal in the reagent piston. Chen's approach utilizes the same concept of a single piston cylinder as does Glenn and Downings, et al., but Chen does teach the ability to work with small sample sizes since the disclosure includes a separate small sample piston. One disadvantage of Chen is that movement of the sample piston can dislodge the reagent piston, thereby causing significant volumetric errors in the sample size, and some error in reagent size. A further disadvantage is that a significant volume of reagent is unusable as the reagent piston must stop somewhat short of its cylinder upper end if the sample piston is to function along its full stroke. One more disadvantage is that there are limitations on the diameter of the reagent piston as a consequence of the geometry of the sample piston and its seals. Moreover, the Chen concept appears costly to manufacture and maintain by reason of its complexity. Moreover, Glenn, Downings, et al., and Chen all teach cylinder fastening systems that are manual, requiring some operator dexterity, as opposed to the automatic cartridge attachment means of the present invention.

The present invention offers all of the flexibility of programmable dilutors and dispensers combined with readily removable and storable, extreme accuracy, low cost, simple, fluid cartridges. In the preferred embodiment, a drive motor actually disconnects the cartridge automatically upon command to further simplify operation. In addition, a simple single piston version is offered, primarily for dispensing reagents, which also utilizes the novel automatic cylinder attachment means of the present invention. Accordingly, the present invention offers substantial unique advantages over the prior art that are extremely valuable to the end user or operator. These advantages are described in significant detail in the following section.

SUMMARY OF THE INVENTION

With the foregoing in mind, it is a principal object of the present invention to furnish an advanced fluid handling device that offers extreme flexibility when used for diluting, dispensing, and/or pipeting fluids such as samples and chemical reagents. This flexibility revolves primarily around the readily detachable, self contained fluid cartridges, that, in their preferred embodiment, utilize a plurality of pistons located in separate piston cylinders.

These fluid cartridges can be readily detached for temperature controlled storage, cleaning, replacement by another cartridge containing a different reagent, and the like. Removal and insertion of cartridges is made more convenient since the novel automatic cylinder attachment means is actuated by a piston motor drive in the preferred embodiment. The automatic cartridge attachment means can also be used with a single piston unit if desired, thereby producing a less expensive unit intended for use primarily as a dispenser of reagents or other fluids.

The cartridge pistons remain with the cartridge when it is detached, thus sealing the cylinder for storage. The automatic piston attachment means which connects the piston to a shaft is preferably accomplished with a magnetic coupling, although other means are feasible and have been tested. The cartridge elements in contact with fluid are normally borosilicate glass and Teflon* for maximum chemical compatibility. Seals are normally of Teflon with a resiliently biased backing or expanding member, such as an O-ring or spring, to account for the poor elastic memory of Teflon based materials.

* Teflon is a registered trademark of E. I. Dupont de Nemours & Co.

In the preferred embodiment, discharge and pickup is through a small bore Teflon tube that is affixed to the cartridge by a coupling nut. A spring or O-ring can be used to aid tube sealing if required. The tube is normally at least three feet (1 meter) long to allow for sample or other fluid pickup in the tube, although shorter lengths are feasible with increased tube or probe inside diameters. Actuation of machine functions is normally accomplished by means of a switch located in a hand probe through which the tube passes. It is also feasible to use other fluid pickup and dispensing means. For example, a fixed probe can be attached to the cartridge and an actuation switch could then be located on the main unit body, attached as a separate foot switch, or the like.

In the preferred embodiment, a unique feature is the novel automatic cartridge attachment means. This is preferably a resiliently biased locking element used for cartridge fastening or locking. This assembly includes at least one spring-loaded ball or other element forced into a locking position in a groove or pocket in a portion of the cartridge by a resiliently biased member. For detachment, the main or reagent piston motor forces the resiliently biased member downward, thus releasing the balls and unfastening the cartridge. Force from the same motor separates the magnetic coupling used to affix the reagent piston in place to the motor shaft. Other coupling means for both the cartridge and pistons are feasible, however, the magnetic coupling has been thoroughly tested in full working models by the inventor, has proved most effective, and has received strongly positive operator reviews.

The primary candidates for piston drive means are digital linear actuator motors which utilize a threaded shaft that passes through the motor. This motor concept offers unique installation advantages and results in a compact, low-profile diluter. Controlled electrical pulses applied to these motors result in precise linear movement of the shaft. Electrical control is normally from a microprocessor controller which receives operator programming input from a keyboard, preferably a liquid proof, sealed membrane switch.

During use, the operator inputs a series of program steps which may include pickup (aspiration) of one or more samples, an air gap in the fluid pickup tube, pickup of one or more reagents, and dispensing of diluent (reagent in the main piston cylinder) along with all previous samples and/or reagents picked up in the probe or tube. Filling of the cartridge with reagent is normally accomplished by retracting the main piston with the probe tip immersed in a reagent reservoir, which aspirates reagent back into the cartridge.

Further features include the ability to electronically interface with other instruments or computers and the ability to use simpler "slave" diluters. Such "slave" diluters would not contain the full compliment of electronics as the "stand alone" or primary diluter as generally described herein. Instead, these "slave" diluters receive commands from the primary diluter, or from other instruments or computers. Such "slave" diluters, including motors, cartridges, housing, etc. are comprised of identical components as the primary diluter. Of course, the main body elements of the present invention may also be incorporated into other types of machines.

The invention represents a significant improvement in fluid handling devices. It includes at least one main body element and at least one fluid container, usually including a plurality of pistons acting as fluid pumping means. These pistons are connected to and position controlled by precision distance moving means. The pistons are disposed sealingly within cylinders that are in fluid communication with fluid passage means, such as a tube, whereby piston movement accomplishes fluid pickup and discharge through the fluid passage means or tube. The focus of the improvement is a valveless fluid cartridge assembly having a separate piston cylinder for each piston, which assembly is readily detachable from the main body element in such a way that the separate pistons readily disconnect from the precision distance moving means and remain in the separate piston cylinders when this valveless fluid cartridge assembly is detached from the main body element.

The invention will be better understood upon reference to the drawings and detailed description of the invention which follow in which:

BRIEF DESCRIPTION OF THE DRAWINGS

FIG. 3 is a fractional centerline cross section of the top portion of a fluid cartridge showing the sample piston assembly, diluent or main cylinder, sample cylinder, interconnecting passageways, discharge tube and discharge tube coupling nut.

FIG. 4 is a fragmentary centerline cross section from the left to the center of the drawing, showing automatic cartridge attachment means and cartridge, including main piston assembly in the detached state.

FIG. 5 is also a fragmentary centerline cross section from the right to the center of the drawing including main cartridge assembly in the attached state.

DETAILED DESCRIPTION

With reference to each of the aforementioned figures in turn, and using like numerals to designate similar parts throughout the several views, a preferred embodiment and several alternative embodiments will now be described.

Figure 1:
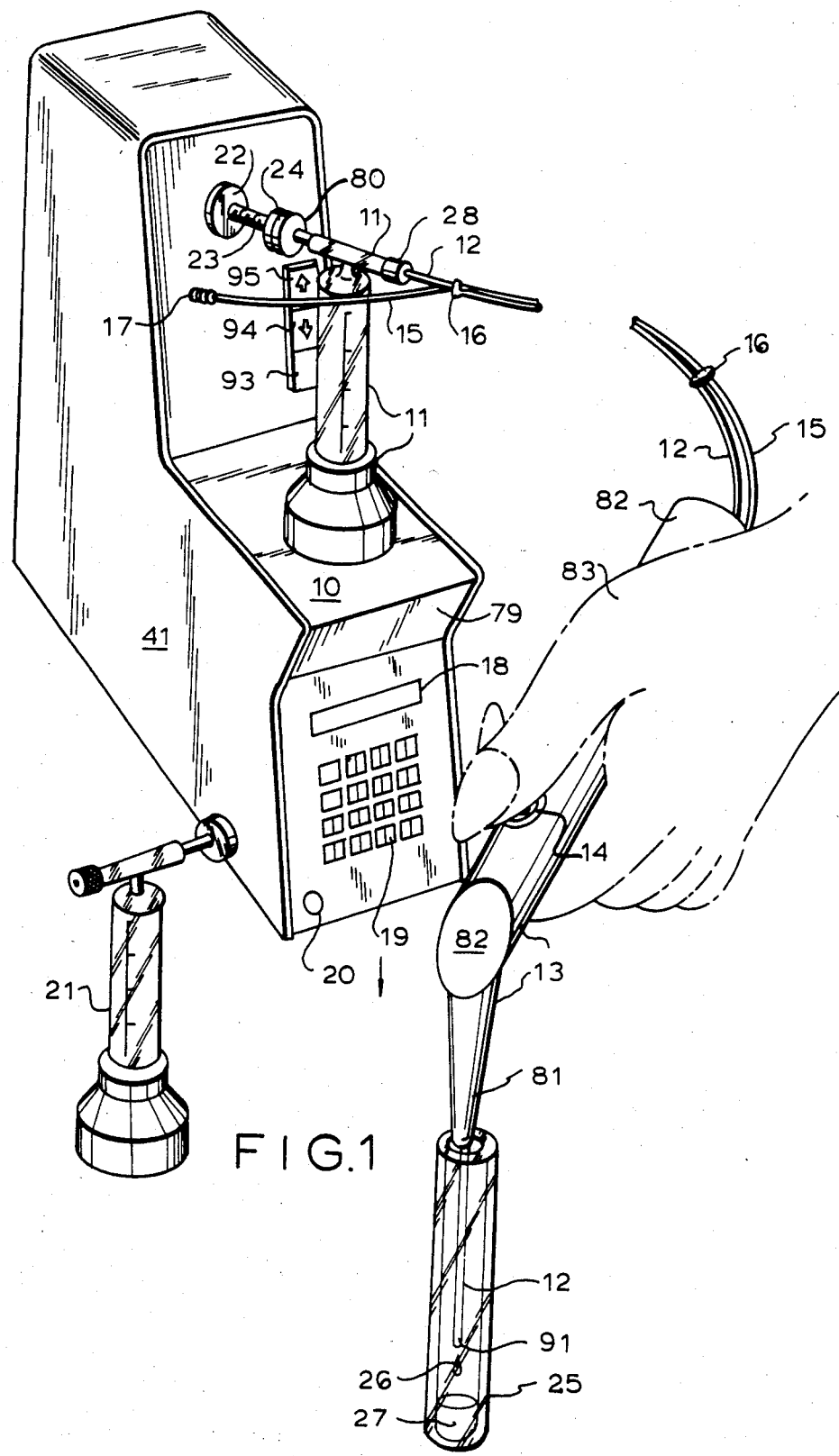
FIG. 1 is a perspective view showing the external working elements of the snap-in cartridge diluter according to the present invention, showing a fluid cartridge coupled in place, programming keyboard, display, control switches, hand probe and discharge tube, stand-alone fluid handling device body element, extra fluid cartridge and the type of receptacle test tube of a type frequently used with the invention.

FIG. 1 discloses a control or "stand alone" snap-in cartridge diluter 10 in the preferred embodiment of the present invention. It shows a cabinet or housing 41, diluter main body element 79, sample piston assembly 80, a readily detachable fluid containing cartridge 11, fluid dispensing tube 12 and tube retaining or coupling nut 28. It also shows an open end 91 of tube 12, electronic wire 15, its connector 17, tubing and wire clamps 16, hand probe 13 and hand probe actuator switch 14. The invention is used generally with a receptacle test tube 25, in which is contained test tube fluid 27, and in which can be seen a dispensed droplet 26. Also shown is an extra cartridge 21 which may be sealed with the air contained therein removed when placed in storage as, for example, in a refrigerated environment to retain diluent such as a reagent, or other fluids. Elements of the diluter 10 to interface with an operator thereof include a status light 20, programmable keyboard 19, function display 18, and release switch 93. Release switch 93 when actuated calls for automatic detachment of the cartridge 11. Also shown are cartridge fill switch 94 and cartridge and tubing prime switch 95. Filling is accomplished by drawing fluid from a separate fluid source through a fluid passageway such as tube 12. Other items shown include the front of the sample piston digital linear actuator motor 22, motor lead screw 23, and magnetic coupling 24. Other types of couplings can, of course, be used besides a permanent magnet as used in the magnetic coupling 24, and these can include both mechanical or electromechanical devices.

During normal operation, numerous diluting, dispensing, pipeting and other functions can be accomplished by means of simple programming of the keyboard 19 or other operator input means. Alternative input means could include rotary knobs although the same are not regarded the design of choice and are not shown. Programmable functions, in addition to numerical, can include such items such as sample volume pickup, air gap, reagent or other fluid volume dispense, reagent or other fluid volume pickup (second, third, etc. reagent picked up in tube 12 through its open end 91), dispense all in the program, ratio calculations, and audible signal such as a bell tone. Also included are store and recall program functions, clear entry and clear program, program, and sequence. The latter allow program monitoring and editing without actually operating the fluid mechanical portions of the diluter 10. A less complex version of the same basic diluter 10 can be made without the programmable capability and would be dedicated to one test procedure only in most cases. This simpler version is, of course, considered within the scope of the present invention.

The preferred embodiment includes fluid passageway or tubing 12, remote hand held probe 13 with its body element 82, tube guide element 81, and actuator switch 14. Also shown is an operator's hand 83. It is possible to use a fixed pickup/discharge tube, simple flexible tube member, or the like, any of which may be attached to the cartridge 11 by a fastener such as coupling nut 28, or other fastening means. These discharge passage variations along with their required actuation means, such as a foot switch or diluter mounted actuator switch, are not shown as they are simple variations well known in the art.

Figure 2:
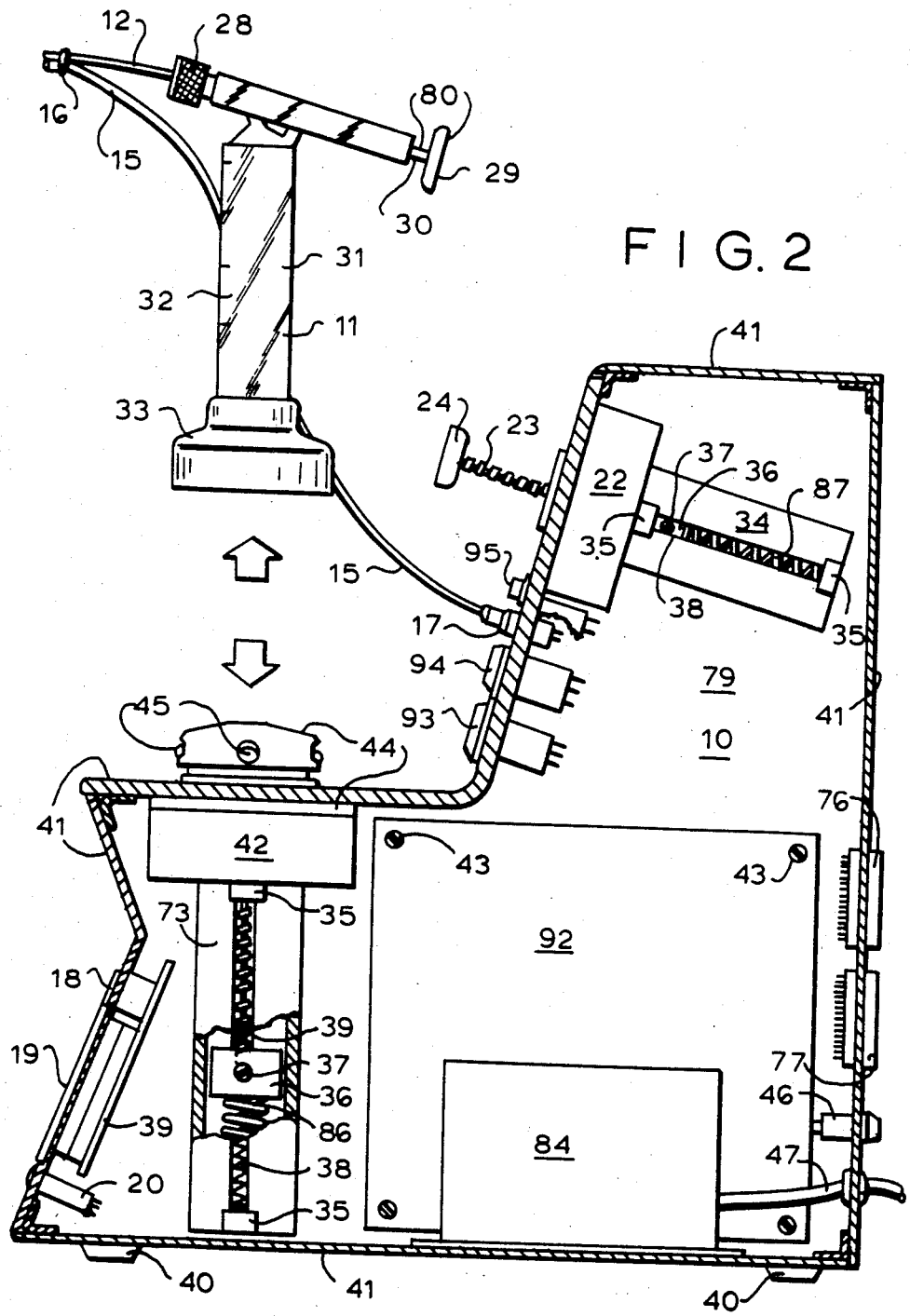
FIG. 2 is a side view of the present invention with a fluid cartridge shown separated from the invention as removed therefrom, and having a side cover removed to show the main piston and sample piston activation motors, and electronic components.

FIG. 2 is a side view of the diluter 10, including housing 41, housing feet 40 and main body element 79. The near side panel has been removed to show the general internal components, less electrical wiring for simplicity, of the diluter 10, with cartridge 11 detached. The preferred embodiment of cartridge 11 includes a glass housing 31, label 32, cartridge base 33, tube nut 28, sample piston shaft 30, plated steel sample piston coupling element 29, and sample piston assembly 80. Also shown attached to the cartridge 11 are tubing 12, electrical wire 15, and electrical connector 17.

Disposed within housing 41 are drive motors 22 and 42 which preferably are digital linear actuator motors with threaded shafts 23 and 39. The digital linear actuator motors 22 and 42 position shafts 23 and 39 outwardly or inwardly in precise incremental amounts by electronic input control means. It is also possible to use other piston drive means such as synchronous or other type motors with shaft position encoders, nonextending shaft stepper motors, solenoid actuators, pneumatic actuators, or other piston movement means although these are not shown. The preferred embodiment digital linear actuator motors 22 and 42 use shaft guide and anti-rotation collar guide passageways 34 and 73, shaft guide collars 36, end travel limit switches 35, and anti-rotation screw pins 37 that slide in slots 38. The reason for the antirotation screw pins 37 and collars 36 is to provide guidance and to prevent rotation of the motor shafts 39 when the motor internal rotor, not shown, rotates, thereby insuring that shaft 39 motions are in axial directions only. Also shown are loading means such as springs 86 and 87, which are used to axially load shafts 39 of motors 22 and 42, thus removing backlash and improving piston positioning accuracy. Loading means such as springs 86 and 87 can alternatively be located in other positions and may be part of the cartridge 11 assembly where said loading means, if located between cartridge housing 31 and sample piston assembly coupling member 29, for example, could also act as a force to hold sample piston assembly 80 in position against sample motor shaft 23 thereby eliminating the need for a coupling magnet 24. The same principle can be applied to the main fluid piston assembly 78 hereinafter described in connection with FIGS. 4 and 5.

Two coupling means are shown in the preferred embodiment. A permanent magnet coupling for the sample piston is comprised of permanent magnet 24 which is removably attached to plated steel sample piston coupling element 29 when in use. A similar coupling is used with the main fluid piston assembly 78 of FIGS. 4 and 5. The other coupling means includes fastener base 44 having balls 45 which interact with cartridge base 33 of cartridge 11.

Other components of this preferred embodiment include a sealed membrane keypad 19, dot matrix light emitting diode (LED) display 18, front panel printed circuit board (PCB) 39, status light 20, main microprocessor mounted PCB 92 and its attachment screws 43, power supply 84, line cord 47, fuse 46 and cartridge release, fill, and prime switches 93, 94 and 95. Also shown are optional connectors 76, 77 such as standard RS 232 ports, each of which generally serve a different purpose. One acts as a jack for input commands from another instrument or computer, and the second relays commands to other slave diluters. The slave diluters, not shown, are similar in appearance and function to the basic control diluter 10 shown. However, they do not normally have a keyboard 19 or display 18 and contain less electronics. These slave diluters, when used, are placed in series with a primary, or control, diluter 10 or other instrument in circumstances when a series of tests and/or different reagents or other fluids are required for a test procedure. It should also be noted that, although only a stand alone version of the diluter 10 is shown, the basic diluter concept shown here can be incorporated into the framework of larger instruments where, in most instances, only the readily detachable fluid cartridge 11 portion of the diluter would be visible to the operator. Further, the vertical orientation of the main diluent piston cylinder and the orientation of the smaller piston cylinder may be varied to accomodate different applications and may, for instance, be horizontal, vertical or at any other angle required.

FIG. 3 shows a centerline cross section view of the preferred embodiment of the top portion of cartridge 11 showing the main reagent or diluent piston cylinder 58, diluent, reagent or other fluid 60, cartridge housing 31 which is preferably of borosilicate glass for chemical resistivity, interconnecting passageway 59 and discharge passageway 65. The latter passageways are normally part of cartridge housing 31 which may be comprised of more than one piece. These may include portions of separate components such as tubing or other elements if desired. Also shown are the sample piston cylinder 61, sample piston assembly 80, sample piston 62 which is normally made of Teflon, sample piston resilient biasing means 63 such as an O-ring or spring, sample piston shaft 30 and piston retaining protrusions such as knobs or rings 64 on sample piston shaft 30. The sample piston assembly 80 normally includes all elements affixed to shaft 30. If driven to the discharge end 65 of piston cylinder 61, sample piston passageway 62 acts as a static seal. Although not shown, another acceptable arrangement utilizes a piston pumping assembly comprised of a precision diameter piston rod that normally has substantial clearance between itself and a piston cylinder 61. Sealing of this moveable piston rod is normally done with a seal fixed in position in the cartridge 11.

Further illustrated in FIG. 3 are means of attaching and sealing a fluid passageway or tube 12 to the cartridge 11. These means may include a threaded bushing 66 affixed to cartridge housing 31, threaded tube nut 28, and resilient compression member 68 which is preferably an O-ring or spring. For storage, with tube 12 removed, a round blank Teflon sealing cover (not shown) is normally inserted under tube coupling nut 28.

During normal operation, the sample piston 62 is retracted to create a suction at the opened end (91 of FIG. 1) of tube 12. With the tube end immersed, this suction aspirates a fluid such as sample or reagent (27 of FIG. 1) from a test tube (25 of FIG. 1) or other container, or air if removed from the liquid, back into tube 12 in a precise amount. When dispensing, the sample piston 62 moves back outward the distance it was retracted. It is also feasible to use this concept without a sample piston cylinder 61 or sample piston 62, in which case the main cylinder 58 and piston assembly (78 of FIG. 4) would handle all fluid 60 pumping functions. In this latter example, with no small sample piston 62 or cylinder 61, the coupling nut assembly 67 is normally concentric with the main reagent piston cylinder 58. Also, the sample piston activation motor (22 of FIG. 2) and its related hardware may be eliminated in such a case.

FIG. 4 displays a fragmentary centerline cross section, taken to the center 74 of the drawing, that shows a preferred design of the cartridge 11 which is fully in position, but wherein the coupling means is retracted. Included are the diluter housing 41, typical attachment screw 70, main motor 42, motor housing 46, motor bearing 47, motor shaft 39, and plated steel piston coupling element 51 that is affixed to the shaft 39 by means of a screw or threads 71. The piston coupling element may include a leak directing lip 75 on its lower edge so that any leakage will be directed to the leakage reservoir 50 in a movable locking means actuation member such as ball actuating cup 48. The ball actuating cup 48 is resiliently loaded upward by biasing member 49, normally a spring. In operation, motor shaft 39 moves outward allowing the ball actuating cup 48 to move upward, which because of sloped outer surfaces forces movable element locking means such as balls 45 outward in track 52 in fastener base 44, thereby locking balls 45 into position in latching pockets or grooves 85 in cartridge base 33. The fastener base 44 is attached to the motor housing 46 by typical screw 69. The cartridge base 33 is either a part of or is rigidly affixed to cartridge 11.

In the preferred embodiment, the main fluid piston assembly 78 is comprised of piston outer housing 55 which is normally made of Teflon and resiliently biased by O-ring or spring 57 and optional magnetic holding insert 54 which contains magnet 53. It is also, of course, possible to utilize other coupling means which may include electromagnets, mechanical or electromechanical means, among others. The diluent piston assembly 78 is disposed within main diluent or reagent piston cylinder 58, which in turn is part of cartridge housing 31 and dispenses precise amounts of a fluid such as the reagent 60 when moved outward. A marking ring 72 is provided in the fastener base 44 so that an operator can detect if cartridge 11 is properly seated on the fastener base 44.

FIG. 5 is a fragmentary cross section mirror image of FIG. 4 up to the center of the drawing 74, except that it shows the cartridge 11 in a coupled or fastened state in which it is firmly locked in position by outwardly disposed balls 45. Shown are all of the same elements as FIG. 4, but with the shaft 39 extended, coupling permanent magnet 53 firmly affixed to plated steel piston coupling element 51 and the outer surfaces of ball actuating cup 48 raised by spring 49 to press outward balls 45 in track 52 and lock them into position in latching pockets or grooves 85 in cartridge base 33.

During normal operation, the main reagent, diluent, or fluid piston assembly 78 is driven outward by motor 42 in precise amounts to dispense a fluid such as diluent or reagent 60. For reagent or other fluid aspiration into tube 12 and/or for cartridge 11 filling, the piston assembly 78 is drawn inward with the open end (91 of FIG. 1) of tube 12 in a fluid. Other elements included in FIG. 5 are main piston cylinder 58, fluid such as reagent 60, main piston assembly 78, piston outer housing 55, piston ring or seal 56, seal resilient compression member 57, permanent magnet housing 54, motor 42, motor housing 46, motor bearing 47, and typical screw 69 that attaches fastener base 44 to motor 42. Although this preferred embodiment shows a novel automatic cylinder attachment means that is completely motor 42 actuated and therefore highly desirable from an operator standpoint, other cartridge 11 fastening means such as hand operated latches, electromechanical latches or the like are considered within the scope of the present invention although they are not illustrated.

While the invention has been described in connection with a preferred and several alternative embodiments, it will be understood that there is no intention thereby to limit the invention. On the contrary, there is intended to be covered all alternatives, modifications and equivalents as may be included within the spirit and scope of the invention as defined by the appended claims, which are the sole definition of the invention.

What is claimed is:

1. In an improved fluid handling device having at least one main body element, fluid passage means, and at least one fluid container that includes a plurality of pistons, the pistons connected to and position controlled by precision distance moving means, said pistons disposed within cylinders that are in fluid communication with the fluid passage means whereby piston movement accomplishes fluid pickup and discharge through the fluid passage means, wherein the improvement comprises:

a valveless fluid cartridge assembly having a separate piston cylinder for each piston, the assembly being readily detachable from the main body element such that the separate pistons disconnect from the precision distance moving means and remain in the separate piston cylinders when the assembly is detached from the main body element.

2. The fluid handling device of claim 1 which further comprises automatic cartridge attachment means.

3. The fluid handling device of claim 2 in which the automatic cartridge attachment means is substantially symmetrical about a centerline of the cartridge.

4. The fluid handling device of claim 2 wherein the automatic cartridge attachment means further comprises:
   a fastener base fixedly attached to the main body element in which is disposed at least one locking means;
   a cartridge base portion of the fluid cartridge assembly, the cartridge base sized for a close fitting relationship with the fastener base and in which is disposed at least one latching pocket for alignment with the locking means; and
   locking means actuator that causes the locking means to move into and out of close fitting relationship with a latching pocket of the cartridge base.

5. The fluid handling device of claim 1 wherein the precision distance moving means is a digital linear actuator motor.

6. The fluid handling device of claim 1 which further comprises a magnetic coupling to connect a piston to precision distance moving means.

7. The fluid handling device of claim 1 which further comprises at least one passageway for fluid interconnection of the separate piston cylinders.

8. The fluid handling device of claim 1 wherein a sealing portion of at least one piston is urged circumferentially outward against a piston cylinder by resilient biasing means.

9. The fluid handling device of claim 1 wherein at least one piston fits freely inside of its cylinder with a piston sealing element fixedly positioned in the cartridge.

10. The fluid handling device of claim 9 wherein the piston sealing element is urged circumferentially inward against the piston.

11. The fluid handling device of claim 1 wherein the precision distance moving means is a motor which includes a shaft passing completely therethrough said movable axially.

12. The fluid handling device of claim 11 which further comprises:
   a shaft guide passageway disposed proximal the shaft,
   a slot in the shaft guide passageway, and
   an anti-rotation member attached to the shaft that travels in the slot to prevent rotation of the axially movable shaft.

13. The fluid handling device of claim 1 wherein the separate piston cylinders are obliquely angled to each other.

14. The fluid handling device of claim 1 wherein the separate piston cylinders are perpendicular to each other.

15. The fluid handling device of claim 1 wherein the separate piston cylinders are parallel to each other.

16. The fluid handling device of claim 1 wherein at least one of the pistons disconnect from the precision distance moving means using a force generated thereby.

17. The fluid handling device of claim 1 wherein the precision distance moving means includes a shaft that is resiliently biased in a shaft axial direction.

18. In an improved fluid handling device having at least one main body element, fluid passage means, and at least one fluid container that includes a plurality of pistons, the pistons connected to and position controlled by precisions distance moving means, said pistons disposed within cylinders that are in fluid communication with the fluid passage means whereby piston movement accomplishes fluid pickup and discharge through the fluid passage means, wherein the improvement comprises:
   a valveless fluid cartridge assembly having a separate piston cylinder for each piston, the assembly being readily detachable from the main body element such that the separate pistons disconnect from the precision distance moving means and remain in the separate piston cylinders when the assembly is detached from the main body element, and
   an automatic cartridge attachment means which includes locking means that is unlocked by a force generated by the precision distance moving means.

19. The fluid handling device of claim 18 in which the automatic cartridge attachment means is substantially symmetrical about a centerline of the cartridge.

20. The fluid handling device of claim 19 wherein the automatic cartridge attachments means further comprises:
   a fastener base fixedly attached to the main body element in which is disposed the locking means;
   a cartridge base portion of the fluid cartridge assembly, the cartridge base sized for a close fitting relationship with the fastener base and in which is disposed at least one latching pocket for alignment with the locking means; and
   locking means actuator that causes the locking means to move into and out of close fitting relationship with a latching pocket of the cartridge base.

21. The fluid handling device of claim 18 wherein the precision distance moving means is a digital linear actuator motor.

22. The fluid handling device of claim 18 which further comprises a magnetic coupling to connect a piston to precision distance moving means.

23. The fluid handling device of claim 18 which further comprises at least one passageway for fluid interconnection of the separate piston cylinders.

24. The fluid handling device of claim 18 wherein a sealing portion of at least one piston is urged circumferentially outward against a piston cylinder by resilient biasing means.

25. The fluid handling device of claim 18 wherein at least one piston fits freely inside of its cylinder with a piston sealing element fixedly positioned in the cartridge.

26. The fluid handling device of claim 25 wherein the piston sealing element is urged circumferentially inward against the piston.

27. The fluid handling device of claim 26 which further comprises a shaft guide passageway disposed proximal the shaft,
   a slot in the shaft guide passageway, and
   an anti-rotation member attached to the shaft that travels in the slot to prevent rotation of the axially movable shaft.

28. The fluid handling device of claim 18 wherein the precision distance moving means is a motor which includes a shaft passing completely therethrough, said shaft movable axially.

29. The fluid handling device of claim 18 wherein the separate piston cylinders are obliquely angled to each other.

30. The fluid handling device of claim 18 wherein the separate piston cylinders are perpendicular to each other.

31. The fluid handling device of claim 18 wherein the separate piston cylinders are parallel to each other.

32. The fluid handling device of claim 18 wherein at least one of the pistons disconnect from the precision distance moving means using a force generated thereby.

33. The fluid handling device of claim 18 wherein the precision distance moving means includes a shaft that is resiliently biased in a shaft axial direction.

34. In an improved fluid handling device having a main body element, fluid passage means, a detachable fluid cartridge assembly having a piston acting as fluid pumping means, the piston detachably connected to and position controlled by precision distance moving means, said piston disposed within a cylinder that is in fluid communication with the fluid passage means whereby piston movement accomplishes fluid pickup and discharge through the fluid passage means wherein the improvement comprises:
 a fastener base fixedly attached to the main body element in which is disposed at least one locking means, said locking means being unlocked by a force generated by the precision distance moving means;
 a cartridge base portion of the fluid cartridge assembly, the cartridge base sized for a close fitting relationship with the fastener base and in which is disposed at least one latching pocket for alignment with the locking means;
 a locking means actuator that causes the locking means to move into and out of close fitting relationship with the latching pocket of the cartridge base.

35. The fluid handling device of claim 34 in which the automatic cartridge attachment means is substantially symmetrical about a centerline of the cartridge.

36. The fluid handling device of claim 34 wherein the precision distance moving means is a digital linear actuator motor.

37. The fluid handling device of claim 34 which further comprises a magnetic coupling to connect a piston to precision distance moving means.

38. The fluid handling device of claim 34 wherein a sealing portion of the piston is urged circumferentially outward against the cylinder by resilient biasing means.

39. The fluid handling device of claim 34 wherein the piston fits freely inside of the cylinder with a piston sealing element fixedly positioned in the cartridge.

40. The fluid handling device of claim 39 wherein the piston sealing element is urged circumferentially inward against the piston.

41. The fluid handling device of claim 34 wherein the precision distance moving means is motor which includes a shaft passing completely therethrough, said shaft movable axially.

42. The fluid handling device of claim 41 which further comprises a shaft guide passageway disposed proximal the shaft,
 a slot in the shaft guide passageway, and
 an anti-rotation member attached to the shaft that travels in the slot to prevent rotation of the axially movable shaft.

43. The fluid handling device of claim 34 wherein the piston disconnects from the precision distance moving means using a force generated thereby.

44. The fluid handling device of claim 34 wherein the precision distance moving means includes a shaft that is resiliently biased in a shaft axial direction.

45. In an improved fluid handling device having a main body element, fluid passage means, a detachable fluid cartridge assembly having a piston acting as fluid pumping means, the piston detachably connected to and position controlled by precision distance moving means, said piston disposed within a cylinder that is in fluid communication with the fluid passage means whereby piston movement accomplishes fluid pickup and discharge through the fluid passage means wherein the improvement comprises:
 cartridge attachment means and piston attachment means that are both actuated by said precision distance moving means using forces generated thereby.

46. The fluid handling device of claim 45 wherein cartridge attachment means and piston attachment means are both actuated in proximity to each other by movement along its axis of a motor shaft.

47. The fluid handling device of claim 45 in which both the cartridge attachment means and piston attachment means are substantially symmetrical about a centerline of the cartridge.

48. The fluid handling device of claim 45 wherein the precision distance moving means is a digital linear actuator motor.

49. The fluid handling device of claim 45 wherein the piston attachment means is a magnetic coupling.

50. The fluid handling device of claim 45 wherein the precision distance moving means is a motor which includes a shaft passing completely therethrough, said shaft movable axially.

* * * * *